United States Patent [19]

McKenna

[11] Patent Number: 4,997,953

[45] Date of Patent: Mar. 5, 1991

[54] PROCESS FOR PREPARING N,N'-BIS(TETRABROMOPHTHALIMIDE)

[75] Inventor: Michael G. McKenna, Baton Rouge, La.

[73] Assignee: Ethyl Corporation, Richmond, Va.

[21] Appl. No.: 425,111

[22] Filed: Oct. 23, 1989

[51] Int. Cl.$^5$ ............................................. C07D 403/04
[52] U.S. Cl. .................................................... 548/461
[58] Field of Search ................................. 548/461, 475

[56] References Cited

U.S. PATENT DOCUMENTS

| | | | |
|---|---|---|---|
| 2,657,169 | 10/1953 | Ligett et al. | 548/475 |
| 3,873,567 | 3/1975 | Cyba | 548/462 |
| 3,917,642 | 11/1975 | Wolford et al. | 548/431 |
| 4,189,423 | 2/1980 | Kumano et al. | 548/462 |
| 4,720,553 | 1/1988 | Lee et al. | 548/475 |
| 4,894,187 | 1/1990 | Bonnet et al. | 252/609 |

FOREIGN PATENT DOCUMENTS

| | | |
|---|---|---|
| 68699 | 2/1987 | Australia . |
| 19731 | 1/1989 | Australia . |
| 292362 | 11/1988 | European Pat. Off. . |
| 300879 | 1/1989 | European Pat. Off. ............ 548/475 |
| 49-45062 | 4/1974 | Japan . |
| 50-64337 | 5/1975 | Japan . |

OTHER PUBLICATIONS

Chem. Abst., vol. 88, No. 63266d (1977), Japan Kokai 52/92257.

Spatz et al., *Industrial and Engineering Chemistry Product Research and Development*, vol. 8(4) (1969), pp. 397–398.

*Primary Examiner*—Mary E. Ceperley
*Attorney, Agent, or Firm*—E. E. Spielman, Jr.; David E. LaRose

[57] ABSTRACT

This invention concerns a process for producing N,N'-bis(tetrabromophthalimide) by: forming a reaction mass from at least (i) tetrabromophthalic anhydride, (ii) hydrazine or a hydrazine provider compound, and (iii) concentrated sulfuric acid; and maintaining the so-formed reaction mass at a temperature within the range of from about 100° C. to about 300° C. for a period up to about 20 hours.

7 Claims, No Drawings

PROCESS FOR PREPARING N,N'-BIS(TETRABROMOPHTHALIMIDE)

BACKGROUND OF THE INVENTION

This invention relates to a process for preparing a bisimide of the formula,

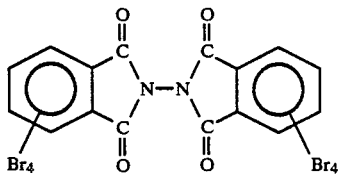

This bisimide has been found to be a useful flame retardant in polyesters, e.g. polybutylene terephthalate, and other resin formulations.

While various processes have been described for the preparation of this bisimide, there is a need for a process which gives the bisimide product in high yield and in highly pure form.

THE INVENTION

N,N'-bis(tetrabromophthalimide) is produced in accordance with this invention by: forming a reaction mass from at least (i) tetrabromophthalic anhydride, (ii) hydrazine or a hydrazine provider compound, and (iii) concentrated sulfuric acid; and maintaining the so-formed reaction mass at a temperature within the range of from about 110° C. to about 300° C. for a time sufficient to obtain a yield of N,N'-bis(tetrabromophthalimide).

The tetrabromophthalic anhydride used in the process of this invention is commercially available from Ethyl Corporation as Saytex ® RB-49 flame retardant and can be obtained in a very pure form, e.g. 99+% pure. From the standpoint of producing a pure N,N'-bis(tetrabromophthalimide) product, the purity of the tetrabromophthalimic anhydride is one important consideration as some of the more common impurities found in tetrabromophthalic anhydride products can be found in the final bisimide product of the process of this invention. If purity of the bisimide product is not a concern to the practitioner, then less pure, say 95% pure, tetrabromophthalic anhydride can be used.

The hydrazine component used to form the reaction mass can be supplied by hydrazine itself or by hydrazine providing compound, i.e., a hydrazine salt, hydrate, etc. which, in the reaction mass environment, will provide hydrazine. Suitable hydrazine providing compounds are hydrazine sulfate, hydrazine hydrate, hydrazine monohydrate, hydrazine dihydrochloride, hydrazine monohydrochloride, hydrazine tartrate, hydrazine acetate, and hydrazine bisulfate. Mixtures of various hydrazine salts, i.e. hydrates, sulfates, acetates, tartrates, hydrochlorides, etc., may also be used. Preferred is hydrazine sulfate.

The concentrated sulfuric acid used in the process of this invention is 90 to 100% sulfuric acid. The commercially available concentrated acids are preferred, e.g. those falling within the range of 93 to 100% sulfuric acid. Some specific examples are, 93%, 96%, 98–99% and 100% sulfuric acid.

In forming the reaction mass, it is convenient to first charge a reaction vessel with a solution of tetrabromophthalic anhydride and a first portion of concentrated sulfuric acid and then adding, to this so-charged solution, a solution comprised of the hydrazine component and a second portion of concentrated sulfuric acid. The first and second portions of concentrated sulfuric acid substantially equal the total acid used in forming the reaction mass. Generally, the first portion will comprise 40% to 60% of the total amount of concentrated sulfuric acid used. In another preferred method of formation, the same solutions are used but the order of addition is reversed. While these methods are preferred, other techniques can be used to form the reaction mass. For example, the hydrazine component can be added neat to a solution comprised of the tetrabromophthalic anhydride and all of the concentrated sulfuric acid to be used in forming the reaction mass.

The total amount of sulfuric acid used in forming the reaction mass is within the range of from about 5 to about 50 moles of acid per mole of tetrabromophthalic anhydride. A preferred amount is within the range of from about 8 to about 12 moles per mole of tetrabromophthalic anhydride.

The reaction mass is formed at a temperature within the range of from about 80° C. to about 270° C. and preferably within the range of from about 100° C. to about 120° C. It is preferred that the molar ratio of tetrabromophthalic anhydride to the hydrazine or hydrazine providing compound used in forming the reaction mass be from about 1:0.6 to about 1:0.8. These ratios provide an excess over the stoichiometric ratio of 1:0.5, which excess is believed to be needed to compensate for loss of available hydrazine in the mass due to hydrazine degradation which occurs under the process conditions. To obtain as pure a product as is possible at the highest yield, the practitioner should adjust this ratio so that the amount of hydrazine available for reaction is as close to the stoichiometric ratio as is conveniently possible. It is possible to use a stoichiometric deficiency or excess of tetrabromophthalic anhydride and still produce a N,N'-bis(tetrabromophthalimide) product, however, the obtained product will contain, respectively, monoimides of hydrazine or tetrabromophthalic anhydride.

After the reaction mass has been substantially formed, the reaction mass is brought to a temperature within the range of from about 110° C. to about 300° C., and preferably to a temperature within the range of from about 170° C. to about 200° C. The reaction mass is maintained at the selected temperature for a period up to about 20 hours and preferably form about 6 to about 4 hours. This period is shorter when using the higher temperatures and longer when using the lower temperatures.

Subsequent to this period, the reaction mass is filtered. The recovered precipitate is then washed to remove the residual sulfuric acid from the precipitate and then dried. The filtration, washing and drying are all done conventionally. The washing medium is preferably water, methanol, acetone, ethanol, or a similar solvent.

The process pressure is preferably atmospheric, however, sub-atmospheric and superatmospheric pressures can be used provided that care is taken to prevent loss of any of the major constituents of the reaction mass.

The equipment in which the process of this invention is carried out should be of materials which can withstand the corrosive nature of the compounds with which it may come into contact. For example, glasslined equipment is especially suitable for the process of this invention.

The following Example illustrates a process of this invention and is not to be taken as limiting the scope of the invention.

EXAMPLE

Preparation of N,N'-Bis(Tetrabromophthalimide)

Into a one-liter resin kettle was charged 481.0 g of Saytex® RB-49 flame retardant (tetrabromophthalic anhydride) and 506 g of 96.7% sulfuric acid. The resultant solution was stirred with a overhead stirrer and heated to 100° C.

Into a 500 mL Erlenmeyer flask was charged 102.8 g hydrazine sulfate and 706 g of 96.7% sulfuric acid. The flask contents were heated and stirred until all of the hydrazine sulfate was dissolved.

The hydrazine sulfate solution was then added dropwise to the resin kettle with a polyethylene pipet over a period of sixty-five minutes to form a reaction mass.

The resulting reaction mass was stirred and heated to 180° C. for 14 hours. The reaction mass was allowed to cool and then subjected to vacuum filtration using a 3-liter funnel (90° C. glass frit) to remove the sulfuric acid. The filter cake was then scraped into a 4-liter beaker containing 3 liters of ice water. The mixture was stirred, allowed to settle, and decanted. The filter cake was returned to the 3-liter funnel, washed and filtered until the supernatant water had a neutral pH. The filter cake was then placed in a large crystallizing dish and dried at 100° C. under vacuum for 24 hours to give 449.5 g of a white solid (94% yield) that had a melting point >500° C. Thermogravimetric Analysis was used to determine the purity of the solid as 95% N,N'-bis(tetrabromophthalimide).

The bisimide products of this invention have an excellent white color, which color is advantageous when the products are used in producing articles which are of a light color or which are white.

I claim:

1. A process for preparing N,N'-bis(tetrabromophthalimide) which comprises: forming a reaction mass from the components consisting essentially of (i) tetrabromophthalic anhydride, (ii) hydrazine or a hydrazine providing compound, and (iii) concentrated sulfuric acid; and maintaining the formed reaction mass at a temperature within the range of from about 110° C. to about 300° C. for a period of time sufficient to obtain a yield of N,N'-bis(tetra-bromophthalimide).

2. The process of claim 1 wherein said hydrazine is provided as a solution of hydrazine sulfate in concentrated sulfuric acid.

3. The process of claim 1 wherein the concentrated sulfuric acid is from about 90% to about 100% sulfuric acid.

4. The process of claim 1 wherein the reaction mass is formed from about 1.67 to about 1.25 moles of tetrabromophthalic anhydride per mole of hydrazine or hydrazine providing compound used in forming the reaction mass.

5. The process of claim 1 wherein said period of time is up to about 20 hours.

6. The process of claim 4 wherein the concentrated sulfuric acid is from about 90% to about 100% sulfuric acid.

7. The process of claim 6 wherein said hydrazine is provided as a solution of hydrazine sulfate in concentrated sulfuric acid.

* * * * *

UNITED STATES PATENT AND TRADEMARK OFFICE
CERTIFICATE OF CORRECTION

PATENT NO. : 4,997,953

DATED : March 5, 1991

INVENTOR(S) : Michael G. McKenna

It is certified that error appears in the above-identified patent and that said Letters Patent is hereby corrected as shown below:

Abstract, line 7 reads "$100^{\circ}C$" and should read -- $110^{\circ}C$ --.

Signed and Sealed this

First Day of September, 1992

Attest:

DOUGLAS B. COMER

*Attesting Officer*  *Acting Commissioner of Patents and Trademarks*